United States Patent
Lee et al.

(10) Patent No.: US 11,549,044 B2
(45) Date of Patent: Jan. 10, 2023

(54) ANTIFREEZING COOLANT COMPOSITION NOT INCLUDING GLYCOL

(71) Applicants: Hyundai Motor Company, Seoul (KR); Kia Motors Corporation, Seoul (KR); KD FINECHEM CO., LTD., Gyeonggi-do (KR)

(72) Inventors: Sung Uk Lee, Chungcheongnam-do (KR); Jin Myeong Park, Busan (KR); Jae Hun Lim, Busan (KR); Hong Ki Lee, Busan (KR)

(73) Assignees: Hyundai Motor Company, Seoul (KR); Kia Motors Corporation, Seoul (KR); KD FINECHEM CO. LTD., Pyeongtaek (KR)

( * ) Notice: Subject to any disclaimer, the term of this patent is extended or adjusted under 35 U.S.C. 154(b) by 0 days.

(21) Appl. No.: 17/116,339

(22) Filed: Dec. 9, 2020

(65) Prior Publication Data

US 2021/0189214 A1    Jun. 24, 2021

(30) Foreign Application Priority Data

Dec. 20, 2019 (KR) .................. 10-2019-0171560

(51) Int. Cl.
| | | |
|---|---|---|
| *C09K 5/10* | (2006.01) | |
| *C09K 5/20* | (2006.01) | |
| *C07C 233/65* | (2006.01) | |
| *C07C 249/06* | (2006.01) | |
| *C07C 249/08* | (2006.01) | |
| *C23F 11/18* | (2006.01) | |
| *C07D 249/06* | (2006.01) | |
| *C07D 249/08* | (2006.01) | |

(52) U.S. Cl.
CPC .............. *C09K 5/20* (2013.01); *C07C 233/65* (2013.01); *C07D 249/06* (2013.01); *C07D 249/08* (2013.01); *C09K 5/10* (2013.01); *C23F 11/181* (2013.01); *C23F 11/184* (2013.01)

(58) Field of Classification Search
CPC .... C09K 5/00; C09K 5/10; C09K 5/20; C23F 11/08; C23F 11/10; C23F 11/14; C23F 11/141; C23F 11/145; C23F 11/146; C23F 11/148; C23F 11/149; C23F 11/184; C07C 233/64; C07C 233/65; C07C 233/76; C07D 249/00; C07D 249/02; C07D 249/04; C07D 249/06; C07D 249/08; C07D 249/16; C07D 249/18

See application file for complete search history.

(56) References Cited

U.S. PATENT DOCUMENTS

| | | | | |
|---|---|---|---|---|
| 5,104,562 A | * | 4/1992 | Kardos .................... | C09K 5/20 252/75 |
| 7,588,695 B2 | * | 9/2009 | Wenderoth .............. | C23F 11/10 252/75 |
| 7,704,406 B2 | * | 4/2010 | Wenderoth .............. | C23F 11/08 252/71 |
| 7,927,505 B2 | * | 4/2011 | Kormann ................. | C09K 5/10 252/74 |
| 8,333,904 B2 | * | 12/2012 | Wenderoth ............ | C23F 11/164 252/73 |
| 2020/0017745 A1 | * | 1/2020 | Dietl ....................... | C09K 5/20 |

FOREIGN PATENT DOCUMENTS

| | | | | |
|---|---|---|---|---|
| EP | 0306972 B1 | 6/1992 | | |
| KR | 100597054 B1 | 7/2006 | | |
| KR | 101061837 B1 | 9/2011 | | |
| WO | WO-2018172064 A1 | * 9/2018 | ............... | C09K 5/20 |

\* cited by examiner

*Primary Examiner* — Matthew R Diaz
(74) *Attorney, Agent, or Firm* — Fox Rothschild LLP

(57) ABSTRACT

Disclosed is an antifreezing coolant composition, which does not include glycol but includes environmentally friendly materials, such as a carboxylic acid salt, an anthranilamide compound, a corrosion inhibitor and a triazole compound. The antifreezing coolant composition may form a thin film on the metal surface in cooling systems for vehicles to thereby exhibit high corrosion resistance at low and high temperatures, superior antifreezing performance at low temperatures, and superior cooling performance at high temperatures.

9 Claims, No Drawings

ANTIFREEZING COOLANT COMPOSITION NOT INCLUDING GLYCOL

CROSS REFERENCE TO RELATED APPLICATION

The present application claims priority based on Korean Patent Application No. 10-2019-0171560, filed on Dec. 20, 2019, the entire content of which is incorporated herein for all purposes by this reference.

TECHNICAL FIELD

The present invention relates to an antifreezing coolant composition, which does not include glycol but includes environmentally friendly materials such as a carboxylic acid salt, an anthranilamide compound, a corrosion inhibitor and a triazole compound.

BACKGROUND

An antifreeze solution is generally made by the addition of glycol or alcohol in order to exhibit antifreezing performance. Glycol and alcohol are liquids that mix well due to the high affinity with water, have antifreezing performance and are colorless and odorless. In particular, ethylene glycol, which is widely used for an antifreeze solution or a coolant solution, exhibits antifreezing performance at a temperature of −50° C. when mixed with water. However, glycol and alcohol are flammable liquids that may cause fires and explosions, and are toxic. Conventional mass use of glycol and alcohol is very burdensome on the environment and adversely affects the environment and ecosystem when entering streams, seas, lakes and rivers.

In order to solve the above problems, an environmentally friendly antifreeze solution from which glycol is partially or completely removed has been developed. The environmentally friendly antifreeze solution, which is useful as a freezing-point depression agent, has high corrosion resistance at low temperatures, but resistance to corrosion of metal materials at high temperatures is significantly decreased. In particular, there is a problem of strong corrosion of iron-containing metal and solder materials.

Therefore, in the case of environmentally friendly antifreeze solutions, it is necessary to develop an antifreezing coolant composition having superior cooling properties and high corrosion resistance even at high temperatures.

SUMMARY OF THE INVENTION

In preferred aspects, provided is an antifreezing coolant composition, which does not include glycol and includes environmentally friendly components, such as a carboxylic acid salt, an anthranilamide compound, etc and the like. The antifreezing coolant composition may form a thin film on the surface of a metal for use in cooling systems for vehicles to thereby exhibit high corrosion resistance at low and high temperatures.

The objectives of the present invention are not limited to the foregoing, and will be able to be clearly understood through the following description and to be realized by the means described in the claims and combinations thereof.

In an aspect, provided is an antifreezing coolant composition that may include 1) an aliphatic or aromatic carboxylic acid salt, and 2) an anthranilamide compound including a compound represented by the following Chemical Formula 1:

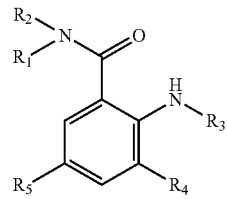

[Chemical Formula 1]

in which $R_1$, $R_2$ and $R_3$ are hydrogen or $C_1$-$C_4$ alkyl and $R_4$ and $R_5$ are hydrogen, fluorine, chlorine, bromine, iodine, methyl, trifluoromethyl or trifluoromethoxy.

Preferred antifreezing coolant compositions may further comprise one or more of a corrosion inhibitor, an aqueous solvent, a triazole compound, and/or a buffer agent.

A term "aliphatic" refers to a saturated or unsaturated hydrocarbon that includes linear, branched or cyclic hydrocarbon without occurrence of π-conjugation or π-conjugated ring (e.g., benzene or aromatic ring). The aliphatic group includes an alkyl, alkenyl, or cycloalkyl groups.

A term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

A term "aromatic" refers to a cyclic or ring structured compound (e.g., aromatic hydrocarbon, aryl, or heteroaryl) that include π-conjugation or π bonding resonance between atoms on the ring structure. The aromatic group includes "aryl" groups that is polyunsaturated, aromatic, hydrocarbon substituent or "heteroaryl" groups that is aryl groups (or rings) that contain at least one heteroatom such as N, O, or S, which can be a single ring or multiple rings (preferably from 1 to 3 rings) that are fused together (i.e., a fused ring aryl) or linked covalently.

A term "carboxylic acid salt" as used herein refers to a compound including at least one carboxyl group (—C(O)O—) and a counter cation such as metal ion or organic or inorganic cation. The carboxylic acid salt may have a genera formula [R—(COO⁻)]$_n$M, wherein M is the cation and n is an integer of 1-3. In certain preferred embodiments, the R may be one or more of the aliphatic and aromatic group described above.

The antifreezing coolant composition may include an amount of about 20 to 50 wt % of the aliphatic or aromatic carboxylic acid salt, an amount of about 0.01 to 1.0 wt % of the anthranilamide compound, and if present an amount of about 0.01 to 1.0 wt % of the corrosion inhibitor, an amount of about 0.01 to 0.5 wt % of the triazole compound, an amount of about 40 to 80 wt % of the aqueous solvent, and an amount of about 0.05 to 0.5 wt % of the buffer agent, all the wt % based on the total weight of the antifreezing coolant composition.

The aliphatic or aromatic carboxylic acid salt may include an alkali metal salt or alkaline earth metal salt.

The aliphatic carboxylic acid may include formic acid, acetic acid, or combinations thereof.

The alkali metal may include potassium (K), sodium (Na), or combinations thereof.

The alkaline earth metal may include magnesium (Mg), calcium (Ca), or combinations thereof.

The corrosion inhibitor may include one or more selected from the group consisting of sodium nitrate ($NaNO_3$), sodium nitrite ($NaNO_2$), phosphoric acid ($H_3PO_4$), and salts thereof.

The triazole compound may include one or more selected from the group consisting of benzotriazole, tolyltriazole, and 1,2,4-triazole.

The buffer agent may include potassium hydroxide (KOH), sodium hydroxide (NaOH), or combinations thereof.

Further provided is a cooling system of a vehicle including the antifreezing coolant composition described herein. Preferably, the antifreezing coolant composition may form a film on a metal surface of the cooling system.

According to various embodiments of the present invention, the antifreezing coolant composition does not use glycol and includes a carboxylic acid salt and an anthranilamide compound and thus can be utilized as an environmentally friendly composition. Also, the antifreezing coolant composition according to various embodiments of the present invention may form a thin film on a metal surface in cooling systems for vehicles to thereby exhibit high corrosion resistance at low and high temperatures, superior antifreezing performance at low temperatures, and superior cooling performance at high temperatures.

Other aspects of the invention are disclosed infra.

DETAILED DESCRIPTION

The above and other objectives, features and advantages of the present invention will be more clearly understood from the following preferred embodiments taken in conjunction with the accompanying drawings. However, the present invention is not limited to the embodiments disclosed herein, and may be modified into different forms. These embodiments are provided to thoroughly explain the invention and to sufficiently transfer the spirit of the present invention to those skilled in the art.

It will be understood that the terms "comprise", "include", "have", etc., when used in this specification, specify the presence of stated features, integers, steps, operations, elements, components, or combinations thereof, but do not preclude the presence or addition of one or more other features, integers, steps, operations, elements, components, or combinations thereof.

Unless otherwise specified, all numbers, values, and/or representations that express the amounts of components, reaction conditions, polymer compositions, and mixtures used herein are to be taken as approximations including various uncertainties affecting measurements that essentially occur in obtaining these values, among others, and thus should be understood to be modified by the term "about" in all cases. Furthermore, when a numerical range is disclosed in this specification, the range is continuous, and includes all values from the minimum value of said range to the maximum value thereof, unless otherwise indicated. Moreover, when such a range pertains to integer values, all integers including the minimum value to the maximum value are included, unless otherwise indicated.

An antifreezing coolant composition ("composition") may include an aliphatic or aromatic carboxylic acid salt in an alkali metal salt or alkaline earth metal salt form, an anthranilamide compound including a compound represented by Chemical Formula 1 below, a corrosion inhibitor, water, a triazole compound and a buffer agent.

[Chemical Formula 1]

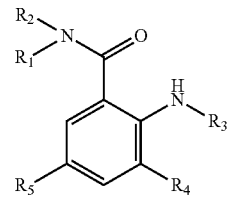

In Chemical Formula 1, $R_1$, $R_2$ and $R_3$ are hydrogen or $C_1$-$C_4$ alkyl, and $R_4$ and $R_5$ are hydrogen, fluorine, chlorine, bromine, iodine, methyl, trifluoromethyl or trifluoromethoxy.

The antifreezing coolant composition may include an amount of about 20 to 50 wt % of the aliphatic or aromatic carboxylic acid salt in an alkali metal salt or alkaline earth metal salt form, an amount of about 0.1 to 1.0 wt % of the anthranilamide compound, and if present an amount of about 0.1 to 1.0 wt % of the corrosion inhibitor, an amount of about 0.01 to 0.5 wt % of the triazole compound, an amount of about 40 to 80 wt % of water, and an amount of about 0.05 to 0.5 wt % of the buffer agent, based on the total weight of the composition. The amount of each component of the antifreezing coolant composition is represented based on 100 wt % of the antifreezing coolant composition unless otherwise indicated.

(1) Aliphatic or Aromatic Carboxylic Acid Salt

The aliphatic or aromatic carboxylic acid salt is not particularly limited, may include an environmentally friendly material and impart not only antifreezing performance and cooling performance but also corrosion resistance to an antifreezing coolant composition including the same.

The aliphatic or aromatic carboxylic acid salt may include an organic carboxylic acid salt usable in the present invention. Although not limited to a specific carboxylic acid salt, preferably useful is the following product.

The aliphatic or aromatic carboxylic acid salt may be produced by treating an aliphatic or aromatic carboxylic acid with an alkali metal or an alkaline earth metal, and is preferably an aliphatic or aromatic carboxylic acid salt in an alkali metal salt or alkaline earth metal salt form.

The alkali metal with which the carboxylic acid is treated may include lithium, sodium, potassium, rubidium, and the like. Also, the alkaline earth metal with which the carboxylic acid may be treated may be beryllium, magnesium, calcium, strontium, barium, and the like. In order to impart superior antifreezing performance and cooling performance and high corrosion resistance, sodium or potassium may preferably be used as the alkali metal, and magnesium (Mg) or calcium (Ca) may preferably be used as the alkaline earth metal.

The carboxylic acid that is treated with the metal may include aliphatic or aromatic carboxylic acid. The aliphatic carboxylic acid may include formic acid, acetic acid, butanoic acid, pentanoic acid, hexanoic acid, 2-ethylhexanoic acid, heptanoic acid, octanoic acid, neo-octanoic acid, nonanoic acid, decanoic acid, neodecanoic acid, undecanoic acid, dodecanoic acid, etc. Also, the aromatic carboxylic acid may be benzoic acid, methyl benzoic acid, ethyl benzoic acid, tertbutyl benzoic acid, cinnamic acid, phthalic acid, terephthalic acid, isophthalic acid, dicyclopentadiene dicarboxylic acid, 2-methylsuccinic acid, 2-methyladipic acid, and the like. In order to impart superior antifreezing performance and cooling performance and high corrosion resistance, formic acid or acetic acid is preferably used as the aliphatic carboxylic acid.

Preferably, in order to impart superior antifreezing performance and cooling performance and high corrosion resistance, an aliphatic carboxylic acid salt in an alkali metal salt form may be used, examples of which include HCOONa, HCOOK, $CH_3COONa$, and $CH_3COOK$.

The amount of the aliphatic carboxylic acid salt in an alkali metal salt form may be about 20 to 50 wt % based on a total of 100 wt % of the antifreezing coolant composition. When the amount of the aliphatic carboxylic acid salt is less than about 20 wt %, the resulting composition shows a freezing temperature that is not appropriate for use as an antifreeze solution. On the other hand, when the amount thereof is greater than about 50 wt %, the resulting composition may show heat transfer performance insufficient for use as an antifreeze solution.

(2) Anthranilamide Compound

The anthranilamide compound is not particularly limited, may include an environmentally friendly material and impart not only antifreezing performance and cooling performance but also corrosion resistance to an antifreezing coolant composition including the same.

The anthranilamide compound may include a compound represented by Chemical Formula 1 below.

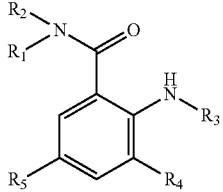

[Chemical Formula 1]

Here, $R_1$, $R_2$ and $R_3$ are hydrogen or $C_1$-$C_4$ alkyl, and preferably hydrogen or methyl. $R_4$ and $R_5$ are hydrogen, C1-C4 alkyl, halogen-substituted C1-C4 alkyl, C1-C4 alkoxy, halogen-substituted C1-C4 alkoxy, or halogen, and preferably hydrogen, methyl, trifluoromethyl, trifluoromethoxy, fluorine, chlorine, bromine or iodine.

The amount of the anthranilamide compound according to the present invention may be about 0.01 to 1.0 wt %, and preferably about 0.05 to 1.0 wt %, based on a total of 100 wt % of the antifreezing coolant composition. When the amount of the anthranilamide compound is less than about 0.01 wt %, it is difficult to ensure antirust performance. On the other hand, when the amount thereof is greater than about 1.0 wt %, precipitation may occur, which is undesirable.

(3) Corrosion Inhibitor

The corrosion inhibitor is not particularly limited, and may include a component for preventing corrosion of copper-like parts, such as aluminum, iron, steel, brass, copper, etc., for use in an antifreeze cooling system.

The corrosion inhibitor may be a typical corrosion inhibitor usable in the antifreezing coolant composition described herein, for example, an inorganic corrosion inhibitor such as sodium nitrate ($NaNO_3$), sodium nitrite ($NaNO_2$), phosphoric acid ($H_3PO_4$), sodium molybdate ($NaMoO_4$), and the like, or an organic corrosion inhibitor such as benzoic acid ($C_6H_5COOH$), sodium benzoate ($C_6H_5COONa$), and the like. Although not limited to a specific corrosion inhibitor, preferably useful is an inorganic corrosion inhibitor, which is easily soluble in an aqueous solvent and may exhibit high resistance to corrosion of iron-containing metals when added in a small amount, particularly one or more selected from the group consisting of sodium nitrate ($NaNO_3$), sodium nitrite ($NaNO_2$), phosphoric acid ($H_3PO_4$), and salts thereof.

The amount of the corrosion inhibitor may be about 0.01 to 1.0 wt %, and preferably about 0.05 to 1.0 wt %, based on a total of 100 wt % of the antifreezing coolant composition. When the amount of the corrosion inhibitor is less than 0.01 wt %, it is difficult to ensure antirust performance. On the other hand, when the amount thereof is greater than about 1.0 wt %, precipitation may occur, which is undesirable.

(4) Triazole Compound

The triazole compound is not particularly limited, and may include a component for preventing corrosion of copper-like parts, such as aluminum, iron, steel, brass, copper, and the like, for use in an antifreeze cooling system.

The triazole compound may be a typical triazole compound usable in the antifreezing coolant composition of the present invention, for example, benzotriazole, tolyltriazole, 1,2,4-triazole, 4-phenyl-1,2,3-triazole, 2-naphthotriazole, 4-nitrobenzotriazole, 2-mercaptobenzothiazole-triazole, etc. Although not limited to a specific triazole compound, benzotriazole, tolyltriazole, 1,2,4-triazole and combinations thereof, which are easily soluble in an aqueous solvent and may exhibit high resistance to corrosion of copper-like parts when added in a small amount, may be preferably used.

The amount of the triazole compound according to the present invention may be about 0.01 to 0.5 wt %, and preferably about 0.05 to 1.0 wt %, based on a total of 100 wt % of the antifreezing coolant composition. When the amount of the triazole compound is less than about 0.01 wt %, it is difficult to ensure antirust performance. On the other hand, if the amount thereof is greater than about 0.5 wt %, precipitation may occur, which is undesirable.

(5) Buffer Agent

The buffer agent is not particularly limited, and may include a material that is able to adjust the pH, preliminary alkalinity, etc. of the antifreezing coolant composition including the same.

The buffer agent may be a typical buffer agent usable in the antifreezing coolant composition of the present invention, for example, potassium hydroxide (KOH), sodium hydroxide (NaOH) or a base compound. Although not limited to a specific buffer agent, potassium hydroxide (KOH) or/and sodium hydroxide (NaOH) may be preferably used to enable appropriate adjustment of the pH of the antifreezing coolant composition according to the present invention.

The amount of the buffer agent according to the present invention may be about 0.05 to 0.5 wt % based on a total of 100 wt % of the antifreezing coolant composition. When the amount of the buffer agent is less than about 0.05 wt %, it is difficult to ensure antirust performance. On the other hand, when the amount thereof is greater than about 0.5 wt %, precipitation may occur, and corrosion of an aluminum material may occur due to a drastic increase in pH, which is undesirable.

(6) Aqueous Solvent

The aqueous solvent is not particularly limited, and may be a solvent component that can mix the components included in the antifreezing coolant composition.

The aqueous solvent may be a aqueous solvent usable in the antifreezing coolant composition of the present invention, for example, water. Although not limited to a specific aqueous solvent, preferably useful is water, which has high specific heat and is environmentally friendly.

The amount of the aqueous solvent may be about 40 to 80 wt % based on a total of 100 wt % of the antifreezing coolant composition. When the amount of the aqueous solvent is less than about 40 wt %, the resulting composition shows heat transfer performance insufficient for use as an antifreeze solution. On the other hand, when the amount thereof is greater than about 80 wt %, the resulting composition shows a freezing temperature that is not appropriate for use as an antifreeze solution.

EXAMPLE

A better understanding of the present invention will be given through the following examples, which are merely set forth to illustrate the present invention but are not to be construed as limiting the scope of the present invention.

Examples 1 to 3 and Comparative Examples 1 to 5: Preparation of Antifreezing Coolant Composition Antifreezing coolant compositions were prepared in a manner in which the components shown in Tables 1 and 2 below were placed in a reactor and mixed at a temperature of 25° C. (room temperature) and a stirrer speed of 100 rpm.

[Individual Components for Antifreezing Coolant Composition]

(1) Aliphatic or aromatic carboxylic acid salt: potassium acetate ($CH_3COO^-K^+$)

(2) Anthranilamide compound: anthranilamide (3) Corrosion inhibitor: sodium nitrite ($NaNO_2$), sodium nitrate ($NaNO_3$), phosphoric acid ($H_3PO_4$)

(4) Triazole compound: benzotriazole, 1,2,4-triazole, tolyltriazole (5) Aqueous solvent: distilled water (6) Buffer agent: potassium hydroxide (KOH), sodium hydroxide (NaOH)

TABLE 1

| Component | Example 1 | Example 2 | Example 3 |
|---|---|---|---|
| Aliphatic or aromatic carboxylic acid salt | 35 | 35 | 35 |
| Anthranilamide compound | 0.05 | 0.5 | 1.0 |
| Corrosion inhibitor | 0.05 | 0.5 | 1.0 |
| Triazole compound | 0.5 | 0.5 | 0.5 |
| Aqueous solvent | 64.05 | 63.15 | 62.15 |
| Buffer agent | 0.35 | 0.35 | 0.35 |
| Additional corrosion inhibitor | — | — | — |

TABLE 2

| Component | Comparative Example 1 | Comparative Example 2 | Comparative Example 3 | Comparative Example 4 | Comparative Example 5 |
|---|---|---|---|---|---|
| Aliphatic or aromatic carboxylic acid salt | 35 | 35 | 35 | 35 | 35 |
| Anthranilamide compound | — | 1.0 | 1.0 | 1.0 | — |
| Corrosion inhibitor | 1.0 | — | 1.0 | — | — |
| Triazole compound | — | — | — | 0.5 | 0.5 |
| Aqueous solvent | 63.65 | 63.65 | 62.65 | 63.15 | 62.65 |
| Buffer agent | 0.35 | 0.35 | 0.35 | 0.35 | 0.35 |
| Additional corrosion inhibitor | — | — | — | — | 1.5 |

Test Example—Evaluation of Antifreezing Coolant Composition for Corrosion of Metal Included in Cooling System for Vehicles The antifreezing coolant compositions of Examples 1 to 3 and Comparative Examples 1 to 5 were evaluated as follows. The results thereof are shown in Table 3 below.

[Evaluation of Corrosion]

Metal specimens were immersed in the antifreezing coolant compositions of Examples 1 to 3 and Comparative Examples 1 to 5, after which corrosion was observed with the naked eye and the weight changes of the specimens were measured.

The testing was performed in accordance with ASTM D 1384, and long-term corrosion resistance was evaluated under conditions of 1000 hr, at a temperature of 88±2° C.×1000 hr (air supply: 100±10 ml/min).

TABLE 3

| Component | Standard (mg) | Example 1 | Example 2 | Example 3 | Comparative Example 1 | Comparative Example 2 | Comparative Example 3 | Comparative Example 4 | Comparative Example 5 |
|---|---|---|---|---|---|---|---|---|---|
| Aluminum | ±30 | −26 | −23 | −17 | −78 | −33 | −37 | −36 | −90 |
| Cast iron | ±10 | −9 | −7 | −6 | −141 | −136 | −151 | −149 | −180 |
| Steel | ±10 | −8 | −6 | −5 | −158 | −145 | −163 | −161 | −195 |
| Brass | ±10 | −8 | −8 | −5 | −26 | −16 | −17 | −16 | −35 |
| Copper | ±10 | −9 | −8 | −6 | −14 | −14 | −13 | −15 | −16 |
| Outer appearance | — | No corrosion | No corrosion | No corrosion | Excessive corrosion in all specimens | | | | |

As shown in Table 3, when the antifreezing coolant compositions, the components and amounts of which satisfy the requirements of the present invention, were used for metal (Examples 1 to 3), the weight changes of all five specimens fell within the standard range, and no corrosion was observed on the outer appearance.

However, when the antifreezing coolant compositions in which any one of the anthranilamide compound, the corrosion inhibitor and the triazole compound was not included, were used for metal or when the additional corrosion inhibitor was used (Comparative Examples 1 to 5), all of the weight changes of the five specimens fell out of the standard range, and corrosion occurred over large portions of the outer surface, indicating that these compositions may be difficult to actually apply to an antifreeze cooling system for vehicles.

Moreover, when the amounts of the anthranilamide compound and the corrosion inhibitor fell out of the ranges of the present invention, the resulting antifreezing coolant composition was not improved compared to Example 3.

Therefore, the antifreezing coolant composition according to various exemplary embodiments of the present invention does not include glycol, but includes the carboxylic acid salt and the anthranilamide compound, and can thus be utilized as an environmentally friendly composition, and can form a thin film on the metal surface in cooling systems for vehicles, thereby exhibiting superior antifreezing performance at low temperatures, superior cooling performance at high temperatures, and high corrosion resistance at both low and high temperatures.

Although the exemplary embodiments of the present invention have been disclosed for illustrative purposes, those skilled in the art will appreciate that various modifications, additions and substitutions are possible without departing from the scope and spirit of the invention as disclosed in the accompanying claims.

What is claimed is:
1. An antifreezing coolant composition, comprising:
an amount of 20 to 50 wt % of an aliphatic or aromatic carboxylic acid salt;
an amount of 0.01 to 1.0 wt % of an anthranilamide compound comprising a compound represented by Chemical Formula 1;
an amount of 0.01 to 1.0 wt % of a corrosion inhibitor;
an amount of 40 to 80 wt % of an aqueous solvent;
an amount of 0.01 to 0.5 wt % of a triazole compound; and
an amount of 0.05 to 0.5 wt % of a buffer agent;
all the wt % are based on the total weight of the antifreezing coolant composition;

[Chemical Formula 1]

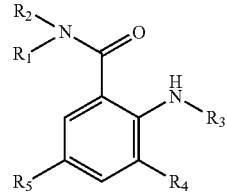

wherein $R_1$, $R_2$ and $R_3$ are hydrogen or $C_1$-$C_4$ alkyl, and $R_4$ and $R_5$ are hydrogen, methyl, trifluoromethyl, trifluoromethoxy, fluorine, chlorine, bromine or iodine,
wherein the buffer agent comprises potassium hydroxide (KOH), sodium hydroxide (NaOH), or combination thereof.

2. The antifreezing coolant composition of claim 1, wherein the aliphatic carboxylic acid comprises formic acid, acetic acid or combinations thereof.

3. The antifreezing coolant composition of claim 1, wherein the aliphatic or aromatic carboxylic acid salt comprises an alkali metal salt or alkaline earth metal salt.

4. The antifreezing coolant composition of claim 3, wherein the alkali metal comprises potassium (K), sodium (Na), or combinations thereof.

5. The antifreezing coolant composition of claim 3, wherein the alkaline earth metal comprises magnesium (Mg), calcium (Ca), or combinations thereof.

6. The antifreezing coolant composition of claim 1, wherein the corrosion inhibitor comprises one or more selected from the group consisting of sodium nitrate ($NaNO_3$), sodium nitrite ($NaNO_2$), phosphoric acid ($H_3PO_4$), and combinations thereof.

7. The antifreezing coolant composition of claim 1, wherein the triazole compound comprises one or more selected from the group consisting of benzotriazole, tolyltriazole, 1,2,4-triazole, and combinations thereof.

8. A cooling system of a vehicle comprising the antifreezing coolant composition of claim 1.

9. The cooling system of claim 8, wherein the antifreezing coolant composition forms a film on a metal surface of the cooling system.

\* \* \* \* \*